(12) United States Patent
Kobayashi et al.

(10) Patent No.: US 6,416,766 B1
(45) Date of Patent: *Jul. 9, 2002

(54) SLURRY COMPOSITION FOR COSMETIC PRODUCT AND METHOD OF USE

(75) Inventors: Masaru Kobayashi, Woodstock; Shigeru Kishida, Storrs, both of CT (US); Isao Imai, Saitama (JP); Heidi A. Radcliffe, Pomfret Ctr., CT (US)

(73) Assignee: U.S. Cosmetics Corporation, Dayville, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/299,846

(22) Filed: Apr. 26, 1999

Related U.S. Application Data

(63) Continuation-in-part of application No. 08/658,461, filed on Jun. 5, 1996, now Pat. No. 5,897,868.

(51) Int. Cl.$^7$ .......................... A61K 7/00; A61K 7/021; A61K 7/42
(52) U.S. Cl. .......................... 424/401; 424/69; 424/59; 424/63; 424/705; 428/403
(58) Field of Search .......................... 424/401, 69, 844, 424/59, 63, 705; 428/403

(56) References Cited

U.S. PATENT DOCUMENTS

| | | | | | |
|---|---|---|---|---|---|
| 4,710,375 A | * | 12/1987 | Takasuka et al. | ............. | 424/69 |
| 4,820,518 A | * | 4/1989 | Murphy et al. | ............. | 424/401 |
| 4,863,800 A | * | 9/1989 | Miyoshi et al. | ............. | 428/403 |
| 4,988,502 A | * | 1/1991 | Ounanian et al. | ............. | 424/63 |
| 5,310,578 A | * | 5/1994 | Thurn-Muller et al. | ..... | 427/220 |
| 5,486,233 A | * | 1/1996 | Mitchell et al. | ............. | 106/416 |
| 5,578,311 A | * | 11/1996 | Nagatani et al. | ............. | 424/401 |

FOREIGN PATENT DOCUMENTS

WO    WO 9415580    *   7/1994

* cited by examiner

*Primary Examiner*—Jose' G. Dees
*Assistant Examiner*—Mina Haghighatian

(57) ABSTRACT

An emulsion slurry for cosmetic products, which comprises particles of pigments d/or extender pigments having a lipophilic moiety attached to the surface thereof and cosmetically acceptable oil component or oily material or combination of both dispersed in a liquid suspending medium comprising a mixture of water and oil.

17 Claims, No Drawings

SLURRY COMPOSITION FOR COSMETIC PRODUCT AND METHOD OF USE

This is a continuation-in-part of application Ser. No. 08/658,461 filed Jun. 5, 1996 now U.S. Pat. No. 5,897,868.

FIELD OF THE INVENTION

The present invention relates to a slurry for preparing cosmetic products and to such cosmetic products made through the use of this slurry. More specifically, the present invention provides a process for preparing smooth, adhesive, spreadable, long-lasting cosmetic products for external use, such as solid or solid-like, cake cosmetic products, such as make-up preparations, as well as liquid cosmetic products such as liquid foundation.

BACKGROUND OF THE INVENTION

Solid or solid-like, cake cosmetic products, such as make up preparations (e.g. face powder, powder foundation, eye shadow, mascara, rouge and the like) are conventionally produced by filling a cosmetic powder into a metal or plastic pan or case followed by molding the powder by a press. In particular, the conventional manufacturing process for preparing cosmetic products includes mixing pigments, and extender pigments and then atomizing them until the colors are well dispersed and uniform. Oily ingredients and auxiliary agents, such as anti-bacterial agents, are added to the pigments and extender pigments and mixed and are atomized to disperse the oily ingredients. The resulting mixture is then screened and further mixed until a uniform cosmetic powder is obtained. The cosmetic powder is filled into a pan or case and molded by a press.

This conventional process has several disadvantages:

i) Pigments and extender pigments have inherent strong hydrophilic properties; thereby, they will fade and/or discolor when contacted by perspiration, unless they are specially treated.

ii) The percentage of out-of-specification product is unacceptably high due to the non-uniformity of surface-color and/or surface-hardness of the molded cosmetic product.

iii) Multi-color molding and complex shape molding are quite expensive because of the cost of the shaping-mold, typically machined from metal.

iv) high labor costs are incurred, arising from the manual labor needed for adjustment and maintenance of equipment and the supply of bulk powder.

v) The loss of cosmetic powder during the molding process is significant.

vi) The work environment is undesirable due to the exposure of the workers to powdery dusty pigments and extender pigments.

It has previously been proposed to use pigments that have been made hydrophobic to solve the problem (i). For example, pigments or extender pigments and/or substrates that are surface-treated with silicone are strongly hydrophobic and can be used to prevent color fading and to improve the duration of use before reapplication. They can also be used for two-way cake (wet/dry application) cosmetics.

While the use of polysiloxanes ameliorates problem (i), the molding process becomes more complex and time consuming, and problems (ii), (iii), (iv), (v), and (vi) remain unsolved.

There have been some suggestions to solve problems (ii), (iii), (iv), (v), and (vi). For example, Japanese Patent 07-29904 and U.S. Pat. No. 4,967,810 suggest the use of a slurry in which pigments, extender pigments and/or substrates, and oily ingredients are dispersed in an organic solvent for injection into the pan or case by an injection machine. These proposals may reduce the severity of problems (ii), (iii), (iv), and (v), but problem (vi) remains unsolved. Further, the choice of usable oily ingredients is restricted depending on the kind or nature of the organic solvent used. For example, non-uniformity of the product is observed when an alcohol is used as the organic solvent with a silicone oil as the oily ingredient of the cosmetic product.

In co-pending parent application 08/658461, a simplified process is described, to decrease the labor intensity of the conventional processes, to improve the work environment, and to provide a smooth, adhesive, spreadable, and long-lasting cosmetic product.

The invention of the parent application was based upon the discovery that when the pigments or extender pigments and/or substrates are made hydrophobic in an aqueous environment with an agent having a lipophilic moiety, such as water-insoluble metal salts of fatty acids, acylamino acids, hydrogenated lecithin, acyl collagen and the like, and rinsed and dried but not completely dried, the pigments remain hydrophilic until full drying. In such state the oily materials are added and the mixture thus formed is kneaded to form an aqueous slurry, the oily materials are uniformly bound to the surface of the pigments and extender pigments and are not disassociated. The parent application thus provided an aqueous slurry for cosmetic products with good dispersal characteristics (without the need for any irritating surfactants for the purpose of dispersing pigments, as is normally required for acceptable dispersal), which comprised particles of pigments and/or extender pigments having a lipophilic moiety attached-to-the surface thereof. This is in contrast to a simple coating (not an attachment) as disclosed in the various Miyoshi U.S. Pat. Nos. 4,606,914, 4,623,074 and 4,863,800, used with the same general materials but which do require the use of surfactants for effecting a dispersion in an aqueous slurry; and a cosmetically acceptable oily ingredient dispersed in a liquid suspending medium consisting essentially of water.

SUMMARY OF THE INVENTION

It is an object of the present invention to improve both the characteristics and economics of the cosmetics made in accordance with the teachings of the parent application by including oily components into the aqueous medium or slurry but without detriment, without the need for surfactants for the purpose of dispersing pigments and whereby processing is also simplified.

It is a further object of the present invention to provide either an oil-in-water slurry composition with a resultant cosmetic having a fresher feel or a water-in-oil slurry composition having a creamier feel and better skin adhesion, with both slurry compositions being well dispersed without surfactants for helping effect such dispersal.

To avoid confusion, as used in the present application, the term "oily materials" refers to oil binders but which are not required to make a slurry during processing. "Oily components" may however be used to improve the quality of a product.

As used in the present application, the term "oily components" refers to oils needed to make the oil phase of an emulsion with at least one "oily component" being required to make the emulsion.

The term "oily ingredients" refers to all other oils such as used in referring to the prior art.

Generally the present invention comprises the aqueous slurry of the parent application made with the hydrophobidized materials, wherein a cosmetically acceptable oily component is included therein as a liquid suspending medium and wherein one of two continuous phases is formed: (a) oil in water (O/W), and (b) water-in-oil (W/O), depending on the relative amounts of oil and water, without the need for inclusion of irritating surfactants for the purpose of maintaining an emulsion by dispersing of the pigment particles. Factors that affect emulsion type include phase volume relations, ingredient interactions, surface characteristics of ingredients as well as other factors.

Pigments and extender pigments that have been hydrophobidized and completely dried have been surprisingly found to be utilizable in making the oil and water slurry emulsion without the necessity for surfactants for the purpose of dispersing pigments (in contrast to the parent application of a fully aqueous slurry wherein the pigments and extender pigments are not fully dried and are still hydrophilic). It is an unexpected discovery wherein a fully hydrophobidized material is acceptably dispersible into a stable emulsion in a slurry containing water and an oil component but without surfactants added for the purpose of dispersing pigments.

As in the parent application the hydrophobidizing agents include silicone, metal soaps and combinations thereof.

With the inclusion of an oil phase, the use of a back injection machine in the processing, as disclosed in the parent application, is not required and the water and oil phase slurry can be used "as is", such as in a liquid foundation.

DETAILED DESCRIPTION OF THE INVENTION

In accordance with the present invention, pigments or extender pigments are made hydrophobic in an aqueous environment with an agent having a lipophilic moiety, such as a water-insoluble polyvalent metal salt of a fatty acid, an acylamino acid, hydrogenated lecithin, acyl collagen or like materials. In particular, the surface of the particles of the pigments and extender pigments carry lipophilic moieties (provided by the fatty acid etc.) linked to the surface of the particles by means of the polyvalent metal. Suitable polyvalent metals include alkaline earth metals, such as magnesium, and calcium, and other polyvalent metals, such as aluminum, titanium, zinc, zirconium and the like. This linking is more than just a coating as takes place in prior art materials such as disclosed in said Miyoshi patents, with resultant differences in dispersion properties as discussed above.

After rinsing and dehydrating the resultant hydrophobic pigment or extender pigment, and with complete drying, suitable oily components or oily materials or the combination of both are added and the mixture is kneaded (oily materials may be, but not necessarily, added to pigment or extender pigment when oily components are added). Thereafter, water and an oily component are added until the resultant oil-in-water or water-in-oil slurry emulsion reaches an appropriate viscosity. This slurry emulsion is then used for the preparation of cosmetic products. The slurry composition may be (but not necessarily) injected into the back of a container for the cosmetic product by an injection machine, while the injected material is vacuum dehydrated via a filter on the top surface of the container. Then the cosmetic product is dried at an appropriate temperature. Alternatively, the slurry composition can be used as is.

The pigments or extender pigments that are made hydrophobic thus carry lipophilic groups on the surface thereof as a result of the treatment with the water-insoluble polyvalent metal salt of the fatty acid or other treating agent. The oily components or oily materials or the combination of both will bind to the lipophilic radicals on the pigments or extender pigments by displacing the water surrounding the treated pigments or extender pigments after the process of rinsing, dehydration, addition of the oily components or oily materials or the combination of both, and kneading (mixing).

The pigments or extender pigments are coated with lipophilic-moieties and surrounding oily component or oily material or the combination of both, and are stable and form fine micelles and become an oil-in-water emulsion slurry without the use of a surfactant (for the purpose of dispersing pigments). The pigments and extender pigments are originally hydrophilic and do not require large energy to be dispersed in the water containing slurry. After the surface treatment, the surface of each particle is coated with lipophilic-moieties and further covered by the surrounding oily component or oily material or the combination of both. Thus, the pigments and extender pigments will not agglomerate and will have excellent dispersibility for cosmetic use.

In a preferred embodiment of the invention, the oil in water slurry consists essentially of from about 10 to about 450%, by weight, of water and from about 1 to about 300%, by weight, of oily component, both based on the weight of the pigment and extender pigment particles. With the preponderance of water in the oil in water slurry, the resultant cosmetic product has a fresher feel. Using the emulsion slurry of the invention including the hydrophobic pigments or extender pigments as described previously, cosmetic products with very intense color tone and without color bleeding can be produced. Moreover, the cosmetic products of the present invention do not exhibit color fading or color bleeding and have excellent skin "feel", adhesiveness, and smoothness compared to cosmetics that use pigments or extender pigments surface-treated in a conventional manner.

The agents useful for imparting hydrophobic properties to the pigments and extender pigments have a lipophilic moiety, and include water-insoluble polyvalent metal salts of fatty acids, acylamino acids, hydrogenated lecithin, acyl collagen and the like. Suitable polyvalent metals include the alkaline earth metals, such as magnesium or calcium, and other metals, such as aluminum, titanium, zinc or zirconium. Surface treatment agents having suitable lipophilic moieties are described in U.S. Pat. Nos. 4,606,914, [4,623,074] 4,622,074 and 4,863,800 and Japanese Patents 60-69011 and 61-73775. The pigments and extender pigments may be made hydrophobic by mixing an aqueous solution of a water-soluble metal salt having a lipophilic moiety with the pigment and extender pigment particles, followed by addition of an aqueous solution of a water-soluble polyvalent metal salt, whereby the lipophilic moiety becomes linked to the particles by means of the polyvalent metal.

The amount of the surface-treating agent used in the present invention is dependent upon the particle size or specific surface area of the pigments or extender pigments being treated. Suitably, the amount of the surface-treating agent is from about 1 to about 20% by weight based on weight of the pigments or extender pigments, preferably from about 2 to about 5% by weight.

Suitable fatty acids providing the lipophilic moiety include lauric acid, myristic acid, palmitic acid, oleic acid, stearic acid, isostearic acid, behenic acid and the like. Water-soluble salts of such fatty acids may be formed with sodium or potassium.

Suitable acylamino acids include N-acyl-L-glutamic acid, N-acyl-N-methylglycine, N-acyl-N-methyl-:β-alanine and the like. The acyl group may include a residue of lauric acid, myristic acid, palmitic acid, oleic acid, stearic acid, isostearic acid, and behenic acid. Water-soluble salts of such acylamino acids may be formed with sodium, potassium or ethanolamine.

Suitable hydrogenated lecithins include (1) hydrogenated natural lecithin obtained by extraction of lecithin from egg yolk, soy bean oil, corn oil, and rapeseed oil followed by hydrogenation; and (2) hydrogenated synthetic lecithin. The iodine value of the hydrogenated lecithin should preferably be less than 30. The term "lecithin" refers to the overall composition; therefore, the lecithin which can be used in the present invention does not have to be pure phosphatidyl choline, but may contain other phospholipids and neutral fats in addition to phosphatidyl choline. Water-soluble salts of the hydrogenated lecithins may be formed with sodium or potassium.

Suitable acyl collagens include those obtained by acylation of an oligopeptide or peptide. Useful oligopeptides or peptides are obtained by partially hydrolyzing protein and/or collagen and have n=1–100. The acyl group may include a residue of lauric acid, myristic acid, palmitic acid, oleic acid, stearic acid, isostearic acid, and behenic acid. Water-soluble salts of such acyl collagens may be formed with sodium or potassium.

The water-soluble salts having a lipophilic moiety used in the present invention are soluble at room temperature or in warm water. When one or more of these salts are added to the pigments and/or extender pigments the lipophilic moiety is adsorbed on the surface of the pigment and/or extender pigment particles. In order to complete the adsorption of the lipophilic moiety, an aqueous solution of a water soluble polyvalent metal salt, such as 1–30% by weight aqueous solution of a water-soluble salt of Al, Mg, Ca, Zn, Zr, or Ti is added in sufficient amount to give a proportion of 1–2 equivalents of the polyvalent metal salt of the fatty acid, acylamino acid, hydrogenated lecithin, or acyl collagen and the like. Useful water-soluble, polyvalent metal salts include aluminum sulfate, aluminum chloride, aluminum nitrate, aluminum potassium sulfate, magnesium sulfate, magnesium chloride, magnesium nitrate, magnesium potassium sulfate, calcium chloride, calcium nitrate, calcium acetate, zinc sulfate, zinc chloride, zinc nitrate, zinc acetate, zirconium sulfate, zirconium chloride, titanium oxysulfate, and titanium chloride. The polyvalent metal salt reacts with the salt of the fatty acid, acylamino acid, hydrogenated lecithin, acyl collagen and the like to form a water-insoluble reaction product which becomes chemically bound onto the surface of the pigment and extender pigment particles.

In addition to the aforementioned hydrophobidizing agents, other suitable hydrophobidizing agents include the following organosilicone compounds, silane coupling agents, and silylating agents:

1. organosilicone compound
    methylhydrogenpolysiloxane
2. silane coupling agent
    vinyltrichlorosilane
    vinyl tris-(beta-methoxy ethoxy) silane
    vinyl triethoxy silane
    vinyl trimethoxy silane
    gamma-methacryloxypropyl trimethoxysilane
    beta-(3, 4-epoxycyclohexyl) ethyl trimethoxysilane
    gamma-glycidoxypropyl trimethoxysilane
    gamma-glycidoxypropyl dimethylethoxysilane
    N-beta-(aminoethyl)-gamma-aminopropyltrimethoxysilane
    N-beta-(aminoethyl)-gamma-minopropylmethyldimethoxysilane
    gamma-aminopropyl triethoxysilane
    N-phenyl-gamma-aminopropyl trimethoxysilane
    gamma-mercapto propyltrimethoxysilane
    gamma-chloropropyl trimethoxysilane
3. silylating agent
    3-a. chlorosilane
        trimethyl chlorosilane
        dimethyl dichlorosilane
        vinyl dimethyl chlorosilane
        trichlorosilane
        vinyltrichlorosilane
    3-b. alkoxysilane
        trimethyl methoxysilane
        dimethyldimethoxysilane
        dimethyldiethoxysilane
    3-c. silazane
        hexamethyl disilazane
    3-d. siloxane
        hexamethyl disiloxane
        octamethyl cyclotetrasiloxane
        alpha-omega-dihydroxy polydimethylsiloxane
    3-e. dimethylpolysiloxy silazane These surface treatment agents are used to hydrophobidize pigments and/or extender pigments prior to making the slurry (pigments are surface treated and dried before going into a slurry). The surface treatment method is the method practiced customarily including spraying the surface treatment agent onto the pigments and grinding the surface treatment agent and pigments in a jet mill as described in JP-Patent Kokoku Publication JP-B-6-59397 (1994), USP# 5,368,639, USP# 5,458,681, and USP# 5,744,126. The amount of the surface treatment agent is 0.1 to 20 wt %.

While some of the hydrophobidizing agents or surface treatment agents such as esters, waxes, fatty alcohols, mineral oils and silicone materials may be considered as surfactants, they are not utilized in accordance with the present invention for the surfactant activities of assisting in distribution of one phase into another, for stabilizing particulate distribution in liquid systems or for reducing interfacial tension between a liquid and a solid. These materials are used strictly for surface treatment and do not function herein as surfactants.

The oily material used in the present invention may be any cosmetically acceptable oily material commonly used in cosmetics, including hydrocarbon compounds, such as dimethicone, cyclomethicone, silicone oil, mineral oil, and squalane, and fatty acids, such as isostearic acid, myristic acid, stearic acid and esters thereof, glycerides, natural fats and oils, and the like. These oily materials may be one oily material or a mixture thereof. The amount of the oily material useful in the present invention is dependent upon the size, specific surface area, or oil absorption of the pigments or extender pigments being treated. Suitably, the amount of the oily material is from about 0 to about 30% by weight of the pigments or extender pigments, preferably from about 2 to about 15% by weight.

Examples of the oily component of the slurry include:

a) Silicone fluids: Methicone; Dimethicone; Cyclomethicone; Phenyl Methicone (Methylphenyl Polysiloxane); and other cosmetically acceptable silicone fluids;

b) Hydrocarbons: Mineral oil; Petrolatum; Isobutane; Isododecane; Isoeicosane; Isohexadecane; Isopentane; Paraffin; Squalane; Squalene; and other cosmetically acceptable hydrocarbons;

c) Vegetable and animal oils: Lanolin oil; Sunflower oil; Caster oil; Olive oil; Wheat germ oil; and other cosmetically acceptable vegetable and animal oils;

d) Esters: Mono-, di-, triglycerides; Octyldodecyl myristate; octyldodecyl oleate; octyldodecyl erucate; octyldodecyl ricinoleate; octyldodecyl laurate; octyldodecyl palmitate; octyldodecyl stearate; octyldodecyl isostearate; Hexyldecyl myristate; hexyldecyl laurate; hexyldecyl palmitate; hexyldecyl stearate; hexyldecyl isostearate; Neopentyl glycol dicaprate; neopentyl glycol diheptanoate; neopentyl glycol diisostearate; neopentyl glycol dilaurate; neopentyl glycol dioctanoate; Trioctanoin; isononyl isononanoate; and other cosmetically acceptable esters;

e) Ethers: Ethylene glycol; propylene glycol; butylene glycol; Polyethylene glycol; polypropylene glycol; and other cosmetically acceptable ethers;

f) Polyols: Glycerin

The amount of oily component needed to make slurry is not less than 1%, and is preferably from 2% to 300%, by weight, with respect to the weight of pigment being dispersed.

The amount of water needed is not less than 10%, and is preferably from 10% to 450%, by weight with respect to the weight of pigment being dispersed. The relative amounts of oily component and water determine if the emulsion is characterized as oil in water or water in oil (with the former providing a fresher feel and the latter providing a creamier feel with better skin adhesion).

The pigments or extender pigments used in the present invention include organic and inorganic pigments, such as titanium dioxide, zinc oxide, zirconium dioxide, yellow iron oxides, black iron oxides, red iron oxides, ultramarine blues, Prussian blues, chromium oxides, chromic hydroxides, and the like, pearlescent pigments, such as mica coated with titanium dioxide, bismuth oxychloride, coal-tar pigments, natural pigments, silica beads, nylon beads, acrylic beads, talc, kaolin, mica, mica-like minerals, such as sericite type materials, magnesium carbonate, calcium carbonate, aluminum silicate, magnesium silicate, calcium silicate and clay and the like.

The most distinctive feature of the present invention is the excellent dispersibility of fine particles or ultra fine pigment or extender pigment particles (those smaller than 1 micron), such as titanium dioxide, zinc oxide, yellow iron oxides, black iron oxides, red iron oxides, ultramarine blues, Prussian blues, chromium oxides, chromium hydroxides or coal tar pigments.

In addition to containing pigments and extender pigments as described above, molding additives may be included depending on the need, to further improve the product quality. These molding additives may be natural cellulose powder, metal soaps, calcium phosphates and like materials used in molding cosmetics or pharmaceuticals. If desired, humectants, binders and/or thickeners may also be used.

The invention is illustrated by means of preferred embodiments in the following examples.

EXAMPLE I (Pressed Make-Up)

The following composition of pigments and extender pigments was mixed using a home type mixer:

| | |
|---|---|
| Talc (silicone treated) | 51.3 g |
| Mica (silicone treated) | 40.0 g |
| Titanium dioxide (silicone treated) | 2.7 g |
| Red iron oxide (silicone treated) | 4.6 g |
| Yellow iron oxide (silicone treated) | 0.9 g |
| Black iron oxide (silicone treated) | 0.5 g |

Each pigment was coated with silicone at a level of 2 weight % relative to the pigment being coated.

The above mixture was added to 200 g of isododecane and 200 g of water (water-in-oil) and mixed until well dispersed (without the use of any surfactants). The resultant slurry was injected into the rear of a pan using the injection machine described in U.S. Pat. No. 4,967,810, while excess isododecane and water needed to make a finished pressed make-up was vacuum extracted from the product from the top of the surface via a filter. The cosmetic product was dried for 8 hours at room temperature. The pressed make-up product obtained had excellent skin feel, skin adhesion, extendibility, payoff and uniformity.

EXAMPLE 2

(Liquid Make-Up)

The following composition of pigments, extender pigments and titanium dioxide was pulverized.

| | |
|---|---|
| Talc (silicone treated) | 9.6 g |
| Titanium dioxide (silicone treated) | 3.6 g |
| Red iron oxide (silicone treated) | 4.8 g |
| Yellow iron oxide (silicone treated) | 1.8 g |
| Black iron oxide (silicone treated) | 0.6 g |

Each pigment was coated with silicone at level of 3.5% (w/w) with respect to the pigment being coated.

The above mixture was added to 39.8 g of cyclomethicone fluid and homogenized until well dispersed. To this, 39.8 g of water was added and homogenized until well dispersed (without the addition of any surfactant). The liquid make-up obtained above had excellent skin feel, skin adhesion, payoff and uniformity in spite of its simple process of manufacture. The stability of the product was excellent.

From the above it is evident that though the hydrophobidized pigments were processed in an oil and water slurry without surfactants (functioning as such), processing was effective in providing cosmetic products having desirable characteristics.

It is understood that the above description is exemplary of the present invention and that changes in components and relative amounts as well as processing steps are possible without departing from the scope of the present invention as defined in the following claims.

What is claimed is:

1. An emulsion slurry for cosmetic products, which comprises fully hydrophobidized particles of pigments and/or extender pigments having a lipophilic moiety attached to the surface thereof and a cosmetically acceptable oily component or oily material or the combination of both, substantially homogeneously dispersed in a liquid suspending emulsion medium comprising an oil component and water, in the absence of materials functioning as surfactants wherein said pigment and/or extender pigment particles have attached to the surface thereof a water insoluble metal salt of a fatty acid, an acylamino acid, a hydrogenated lecithin or an acyl collagen.

2. The emulsion slurry of claim 1 wherein said oily component is selected from the group consisting of cosmetically acceptable silicone fluids, cosmetically acceptable hydrocarbons, cosmetically acceptable vegetable and animal oils, cosmetically acceptable esters, cosmetically acceptable ethers, and polyols.

3. The emulsion slurry according to claim 1, wherein said water-insoluble metal salt is a salt of a polyvalent metal.

4. The emulsion slurry according to claim 3, wherein said polyvalent metal salt is a magnesium, calcium, aluminum, titanium, zinc or zirconium salt.

5. The emulsion slurry according to claim 1, wherein said slurry comprises from about 10 to about 450%, by weight of water, about 1 to about 300% of the oily component and from about 0 to about 30%, by weight, of said oily material, all based on the weight of the pigment and extender pigment particles.

6. A cosmetic product formed by drying the emulsion slurry of claim 1.

7. A cosmetic product formed from the emulsion slurry of claim 1 as is.

8. The cosmetic product of claim 1 wherein the particles of pigments are hydrophobidized by hydrophobidizing agents selected from the group consisting of organosilicone compounds, silane coupling agents, and silylating agents, prior to attaching the lipophilic moiety thereto.

9. A method of preparing the emulsion slurry of claim 1, which comprises dispersing particles of a pigment and/or extender pigment into a liquid suspending medium comprising oil and water in the absence of materials functioning as surfactants, adhering a lipophilic moiety to the surface of said particles while said particles are in an aqueous solution, and admixing any one of a cosmetically acceptable oily component, oily material and combination of both; with said dispersion to form an emulsion slurry.

10. The method of claim 9 wherein the particles of pigments are hydrophobidized by hydrophobidizing agents selected from the group consisting of organosilicone compounds, silane coupling agents, and silylating agents, prior to attaching the lipophilic moiety thereto.

11. A method of preparing the emulsion slurry of claim 1, comprising the steps of forming a dispersion of particles of a pigment or extender pigment in a liquid suspending medium comprising oil and water in the absence of materials functioning as surfactants, adhering a lipophilic moiety to the surface of said particles while said particles are in an aqueous solution, drying said resultant lipophilic moiety-carrying particles, admixing said dried lipophilic moiety-carrying particles with a cosmetically acceptable oily component, oily material or combination thereof with water to form an emulsion slurry comprising said lipophilic moiety-carrying particles and said oily component.

12. The emulsion slurry of claim 2, wherein the cosmetically acceptable silicone fluids are selected from the group consisting of Methicone, Dimethicone, Cyclomethicone, Phenyl Methicone, and Methylphenyl Polysiloxane.

13. The emulsion slurry of claim 2, wherein the cosmetically acceptable hydrocarbons are selected from the group consisting of Mineral oil, Petrolatum, Isobutane, Isododecane, Isoeicosane, Isohexadecane, Isopentane, Paraffin, Squalane, and Squalene.

14. The emulsion slurry of claim 2, wherein the cosmetically acceptable vegetable and animal oils are selected from the group consisting of Lanolin oil, Sunflower oil, Caster oil, Olive oil, and Wheat germ oil.

15. The emulsion slurry of claim 2, wherein the cosmetically acceptable esters are selected from the group consisting of mono-glycerides, di-glycerides, tri-glycerides, Octyldodecyl myristate, octyldodecyl oleate, octyldodecyl erucate, octyldodecyl ricinoleate, octyldodecyl laurate, octyldodecyl palmitate, octyldodecyl stearate, octyldodecyl isostearate, Hexyldecyl myristate, hexyldecyl laurate, hexyldecyl palmitate, hexyldecyl stearate, hexyldecyl isostearate, Neopentyl glycol dicaprate, neopentyl glycol diheptanoate, neopentyl glycol diisostearate, neopentyl glycol dilaurate, neopentyl glycol dioctanoate, Trioctanoin, and isononyl isononanoate.

16. The emulsion slurry of claim 2, wherein the cosmetically acceptable ethers are selected from the group consisting of Ethylene glycol, propylene glycol, butylene glycol, Polyethylene glycol, and polypropylene glycol.

17. The emulsion slurry of claim 2, wherein the polyol is Glycerin.

* * * * *